(12) United States Patent
Calabro' et al.

(10) Patent No.: US 10,595,773 B2
(45) Date of Patent: Mar. 24, 2020

(54) DEVICE FOR CARDIAC ABLATION DESIGNED FOR AUTOMATIC ELECTRONIC CONTROL OF THE ESOPHAGEAL CATHETER POSITION

(71) Applicant: FIAB S.P.A., Vicchio (FI) (IT)

(72) Inventors: Alberto Calabro', Florence (IT); Antonio Fasano, Florence (IT)

(73) Assignee: FIAB S.P.A., Vicchio (IT)

( * ) Notice: Subject to any disclaimer, the term of this patent is extended or adjusted under 35 U.S.C. 154(b) by 212 days.

(21) Appl. No.: 15/359,281

(22) Filed: Nov. 22, 2016

(65) Prior Publication Data
US 2017/0143258 A1    May 25, 2017

(30) Foreign Application Priority Data
Nov. 24, 2015    (IT) .......................... 102015000076140

(51) Int. Cl.
| A61B 5/00 | (2006.01) |
| A61B 18/02 | (2006.01) |
| A61B 18/14 | (2006.01) |
| A61B 5/01 | (2006.01) |
| A61B 17/00 | (2006.01) |
| A61B 18/00 | (2006.01) |

(52) U.S. Cl.
CPC .............. *A61B 5/4836* (2013.01); *A61B 5/01* (2013.01); *A61B 5/015* (2013.01); *A61B 5/687* (2013.01); *A61B 5/6852* (2013.01); *A61B 5/742* (2013.01); *A61B 5/7405* (2013.01); *A61B 5/746* (2013.01); *A61B 17/00234* (2013.01); *A61B 18/02* (2013.01); *A61B 18/1492* (2013.01); *A61B 2017/00101* (2013.01); *A61B 2017/00278* (2013.01); *A61B 2018/00351* (2013.01); *A61B 2018/00577* (2013.01); *A61B 2018/00797* (2013.01); *A61B 2018/00898* (2013.01); *A61B 2018/0212* (2013.01); *A61B 2505/05* (2013.01); *A61B 2562/043* (2013.01)

(58) Field of Classification Search
CPC ......... A61B 5/4836; A61B 5/01; A61B 5/015; A61B 5/687
See application file for complete search history.

(56) References Cited

U.S. PATENT DOCUMENTS

| 9,131,853 | B2 | 9/2015 | Tiano | |
| 9,155,476 | B2 | 10/2015 | Fojtik | |
| 9,668,655 | B2 | 6/2017 | Fojtik | |
| 2008/0215047 | A1 | 9/2008 | Calabro et al. | |
| 2010/0030098 | A1 | 2/2010 | Fojtik | |
| 2013/0006139 | A1* | 1/2013 | Tiano | ..................... A61B 5/015 600/549 |
| 2015/0094570 | A1 | 4/2015 | Fojtik | |
| 2015/0342665 | A1 | 12/2015 | Tiano | |
| 2016/0029897 | A1 | 2/2016 | Fojtik | |

FOREIGN PATENT DOCUMENTS

WO    2009117523    9/2009

* cited by examiner

*Primary Examiner* — Patrick Fernandes
(74) *Attorney, Agent, or Firm* — Pearne & Gordon LLP

(57) ABSTRACT

This invention concerns a device (1) for detecting and monitoring the temperature of the esophagus (E) during cardiac ablation treatments, which makes it possible to continuously and automatically monitor the correct positioning of the temperature sensors (3a, 3b, 3c, 3d, 3e).

9 Claims, 2 Drawing Sheets

DEVICE FOR CARDIAC ABLATION DESIGNED FOR AUTOMATIC ELECTRONIC CONTROL OF THE ESOPHAGEAL CATHETER POSITION

FIELD OF THE INVENTION

This invention concerns a device for the detection and monitoring of the temperature of the esophagus during cardiac ablation treatments, that allows control of the correct positioning of the temperature sensors in the esophagus in a more secure and frequent way compared to prior art devices, and without risks for the patient's health. The control is in fact performed in a continuous and automatic way, thanks to a special electronic apparatus.

DESCRIPTION OF RELATED ART

The purpose of cardiac ablation is the local destruction of electrically active tissues affected by the disease that is responsible for the heart irregularity detected.

Cardiac ablation treatments are performed by heating or by cooling. In the first case, a special catheter is used equipped with an electrode that emits a radiofrequency electromagnetic field. In the second case, in which the ablation treatment is also called cryo-ablation, a balloon that can be inflated with a very low temperature gas is used. During cardiac ablation treatments, it is fundamental to keep a check on the temperature of the tissues surrounding the area of the diseased tissues to be destroyed. These surrounding tissues can be severely and even lethally damaged by excessive heating or cooling. In particular, it has been observed that the esophagus is an organ potentially at risk due to the fact that its anatomical position can be very close to the rear wall of the left atrium, which is usually near the ablation sites.

Prior art devices comprise at least one probe equipped with heat sensors, which vary in number and type. This probe is suitable for insertion in the patient's esophagus and to be positioned in such a way as to detect the temperature in the most critical points. This probe preferably comprises an esophageal catheter, on which these sensors are positioned.

During the ablation procedures performed by heating or by cooling, the catheter may be moved and the sensors may become positioned in such a way as to be unable to detect the maximum and minimum temperatures reached in the esophagus. However, since ablation usually involves various sites, the source of radiofrequency or the cryo-ablator balloon is moved, thus varying its position with respect to the heat sensors of the esophageal probe.

Elements made from material that can be identified by radiography, such as radio opaque material, are currently used to check that the catheter is positioned correctly. These elements are positioned along the catheter and on reciprocally opposite respective parts of the row of sensors, so that the row of sensors is between these elements. The positioning of these elements, radiographically detected, thus indicates the part of the esophagus being monitored by the sensors, so that any incorrect positioning can be corrected.

X-rays can have not insignificant side effects on the health of the patient as well as on the health of the personnel involved in the treatment procedure.

To check the positioning of the sensors with a certain frequency, the patient would have to be bombarded with X-rays an excessive number of times. Prior art monitoring devices thus impose a certain limit on the time frequency with which the positioning of the sensors can be checked.

The aim of this invention is to provide a device for monitoring the temperature of the esophagus during cardiac ablation treatments that makes it possible to check the positioning of the temperature sensors in a continuous and automatic way, and without risks for the health of the patient and the medical personnel.

SUMMARY OF THE INVENTION

This is achieved by means of a device for the detection of the temperature of the esophagus during cardiac ablation treatments,
comprising an esophageal catheter which can be inserted in a patient's esophagus, and comprising three or more temperature sensors designed to detect the temperature of respective portions of the esophagus,
each of these sensors being configured to generate, at successive time points, respective detection signals indicating the temperature of the respective portion of the esophagus,
wherein the sensors are positioned on the catheter and distributed along a prevalent development direction of the catheter between a first sensor and a last sensor,
wherein the device also comprises a control unit that can be connected when in use to the catheter to receive the detection signals emitted by each of the sensors,
characterised in that the control unit is configured to generate at least one alarm signal when, among the temperatures detected by the sensors at the same time point, the maximum (radiofrequency ablation) or minimum (cryoablation) temperature is detected by at least one of these first and last sensors.

In fact, if the maximum (radiofrequency ablation) or minimum (cryoablation) temperature is detected by one of the end sensors, and thus by the first sensor or by the last sensor, this means that the catheter is positioned incorrectly. It has in fact been experimentally detected that the spatial distribution of the temperature along the esophagus presents a maximum or minimum peak, according to whether the ablation treatment is performed by heating or by cooling.

In other words, the fact that the peak is not detected by one of the intermediate sensors, but by one of the end sensors, could indicate that the catheter is not positioned correctly to detect the true maximum or minimum temperature in the esophagus.

A possible embodiment of the invention may comprise at least one of the following technical aspects.

The device preferably comprises at least one acoustic and/or luminous indicator connected to the control unit.

This indicator is designed to be activated by the alarm signal generated by the control unit.

The control unit is preferably configured to compare, for each of the time points, all the detection signals generated by the sensors.

In this way, the control unit can detect whether the maximum or minimum temperature (according to the ablation technique) is detected by at least one of the end sensors. As already mentioned, end sensors mean the first sensor and the last sensor.

The sensors preferably form at least one row of sensors along the catheter development direction.

The sensors that form at least one row of sensors are preferably aligned with each other and parallel to the development direction or along the development direction.

The sensors are preferably equidistant to each other along the catheter development direction.

The distance between one sensor and the next, along the development direction, is preferably between 0.5 cm and 2 cm, and/or less than or equal to 2 cm and/or more than or equal to 0.5 cm.

The distance between the first and the last sensor, along the development direction, is preferably between 3 and 8 cm and/or less than or equal to 8 cm and/or more than or equal to 3 cm.

The catheter is preferably not equipped with ablation elements.

Each sensor is preferably associated with at least one transducer to generate at least the detection signals.

The sensors could also form several rows of sensors along the catheter development direction.

The sensors that form each of these rows are preferably aligned and parallel to the development direction or along the development direction.

The rows are in turn preferably angularly distributed around the development direction.

The control unit is preferably programmed with at least one limit value of the temperature that can be reached by the esophagus.

This limit value is preferably set and memorized in the control unit by a user.

The control unit is preferably configured to generate at least one further alarm signal when at least one temperature detected by at least one of the sensors is equal to or higher than or equal to or lower than a respective preset maximum or minimum limit value, the at least one acoustic and/or luminous indicator being designed to be activated also by the further alarm signal.

The features of this invention are described in detail below, provided as a non-limiting example of the more general concepts claimed.

BRIEF DESCRIPTION OF THE DRAWINGS

The detailed description which follows relates to the accompanying drawings, in which.

DETAILED DESCRIPTION OF PREFERRED EMBODIMENTS OF THE INVENTION

Figure 1:
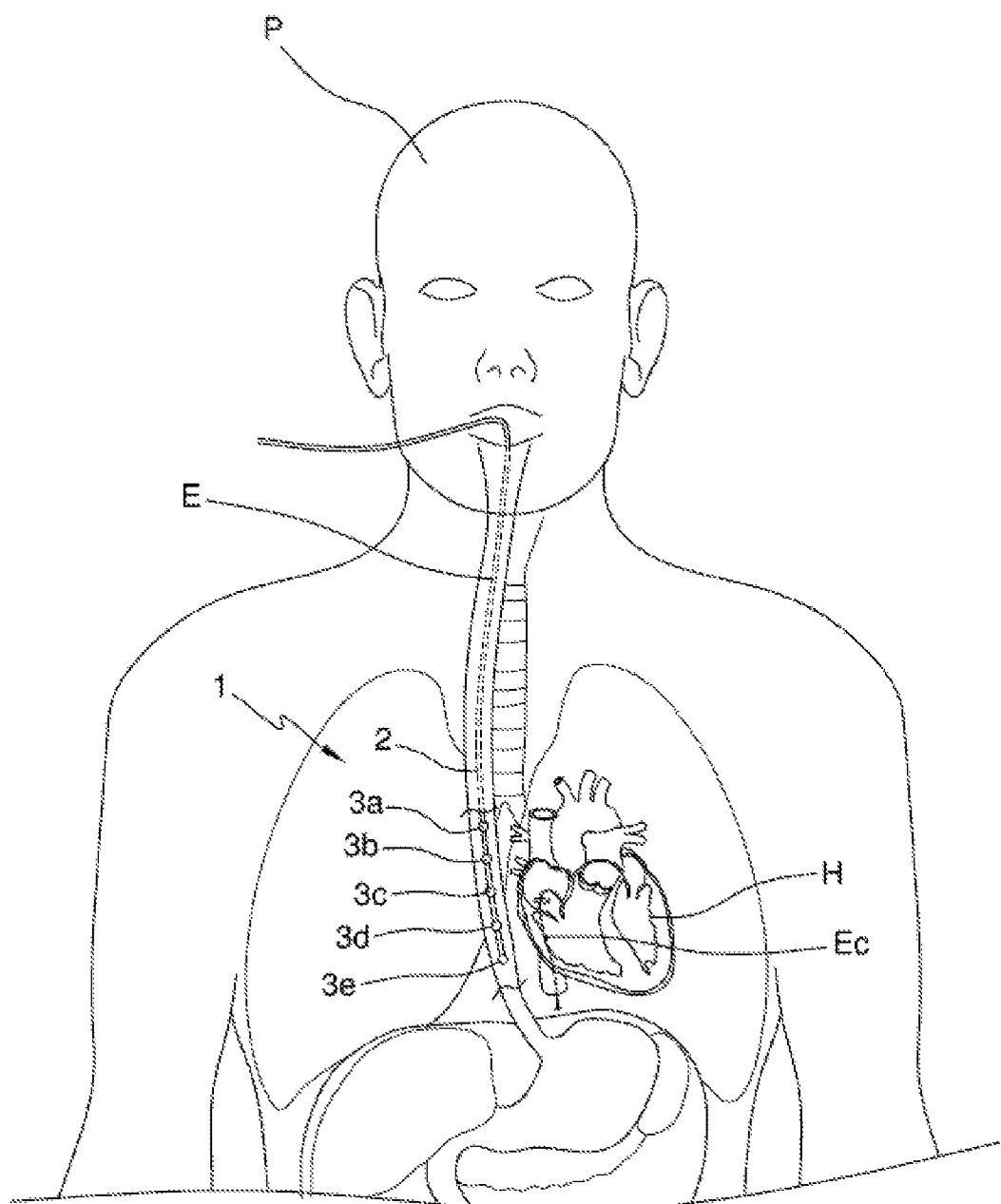
FIG. 1 shows a a part of a possible embodiment of the invention, in a specific operating condition.

FIG. 1 shows a device 1 for detecting the temperature of the esophagus E during cardiac ablation treatments, according to a possible embodiment of the invention. The device 1 comprises an esophageal catheter 2 which can be inserted in the esophagus E of a patient P.

The attached drawings refer to a specific operating condition during which the heart H of a patient P is treated by means of an additional catheter, which can be defined as an electrocatheter Ec.

Figure 2:
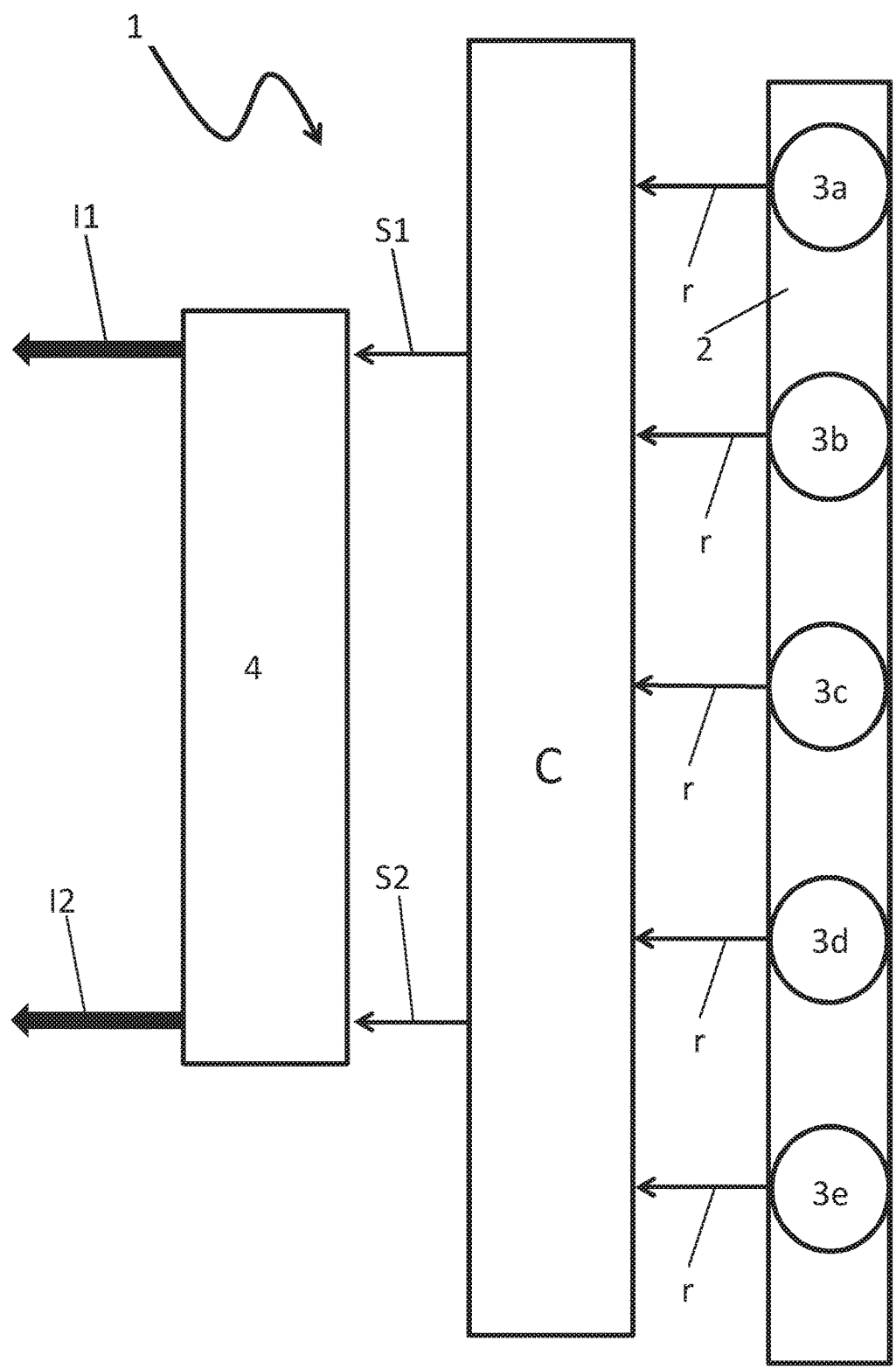
FIG. 2 is a schematic perspective view of this possible embodiment of the invention.

In the operating condition shown in FIGS. 1 and 2, the electrocatheter Ec is used to remove, by means of heating, the diseased tissue responsible for the irregularities of the patient's heart rhythm, indicated with P.

The electrocatheter Ec preferably works on the inner surfaces of the right or left atrium of the heart H of the patient P.

This invention can also be applied in ablation treatments by cooling, also known as cryo-ablation.

In the embodiment shown in the drawings, the device 1 comprises 5 temperature sensors 3*a*, 3*b*, 3*c*, 3*d* and 3*e*, located on the catheter 2. The number of sensors can differ from the number in the embodiment shown, but in other possible embodiments is at least equal to 3.

In the embodiment shown in the drawings, the catheter 2 is advantageously not equipped with ablation elements.

Each of the sensors 3*a*-3*e* is designed to detect the temperature of a respective portion of the esophagus E.

In the embodiment shown in the drawings, the sensors 3*a*-3*e* are located along the catheter 2, so as to be sensitive to the temperature of the respective different parts of the esophagus E. In addition, in the embodiment shown, the sensors 3*a*-3*e* are distributed along the main development direction of the catheter 2.

The sensors are thus distributed between a first sensor 3*a* and a last sensor 3*e*.

In the embodiment shown in the drawings, the sensors 3*a*-3*e* advantageously form at least one row of sensors along the development direction of the catheter 2. The sensors 3*a*-3*e* that form at least one row are advantageously aligned and parallel to the development direction or along the development direction.

The sensors 3*a*-3*e* are shown equidistant to each other along the development direction of the catheter 2, but other arrangements can be adopted in specific embodiments.

Another possible embodiment could comprise several rows of sensors along the development direction of the catheter. These rows could in turn be distributed at angles around the development direction.

In this embodiment, the sensors that form each of these rows would preferably be aligned and parallel to the development direction or along the development direction.

In the embodiment shown, the distance between one sensor and the next, along the development direction, is advantageously between 0.5 cm and 2 cm. The distance between the first sensor 3*a* and the last sensor 3*e* is preferably between 3 and 8 cm.

The arrangement of the sensors 3*a*-3*e* along the catheter 2 can also be seen in FIG. 2. Each of these sensors 3*a*-3*e* is configured to generate, at successive time points, respective indicative detection signals r of the temperature of the respective portion of the esophagus E. These detection signals r are indicated with arrows, in FIG. 2, also to show the route from the sensors 3*a*-3*e* to the control unit C.

Each sensor 3*a*-3*e* is preferably associated with at least one respective transducer, not shown, to generate at least the detection signals r. The combination of at least one sensor and at least one transducer can thus be defined as a temperature detector.

The device 1 also comprises a control unit C that can be connected when in use to the catheter 2. The control unit C is designed to receive, by connection means not shown, the detection signals r coming from each of the sensors 3*a*-3*e*.

The box C shown in FIG. 2 is a block schematically representing the control unit C. In FIG. 2, the catheter 2 is shown in such a way as to reproduce its basic shape, above all with reference to the positioning of the sensors 3*a*-3*e* along the development direction of the catheter 2.

The control unit 2 is preferably programmed with at least one limit value of the temperature that can be reached by the esophagus E. This limit value can be set and memorized in the control unit C by a user.

In the operating condition shown in FIG. 1, this limit value is a maximum value, since the electrocatheter Ec is designed to carry out cardiac ablation treatments by heating.

This temperature limit value could be a minimum value in another operating condition wherein the treatment could be cryo-ablation, and thus ablation by means of cooling.

The control unit C is configured to generate at least one alarm signal S1 when, among the temperatures detected by the sensors 3a-3e at the same time point, the maximum (RF ablation) is detected by at least one of these first sensors 3a and last sensors 3e.

The control unit C is configured to compare, for each of the time points, all the detection signals generated by the sensors 3a-3e.

In order to warn the doctor of the incorrect positioning of the catheter 2, the device 1 comprises at least one acoustic and/or luminous indicator 4. This indicator 4 is connected to the control unit C and designed to be activated by the alarm signal S1 generated by the control unit C.

The indicator 4 can comprise, for example, a monitor and/or an acoustic indicator.

If there are several rows of sensors, in another possible embodiment, the control unit C would be configured to generate at least one alarm signal S1 when, for at least one of these rows of sensors, the maximum temperature is detected by the first sensor of this at least one row or by the last sensor of this at least one row.

In the embodiment shown, the control unit C is preferably also configured to generate at least another alarm signal S2 when at least one temperature detected by at least one of the sensors 3a-3e is higher than or equal to this limit value.

Preferably, to avoid false alarms, the comparison of the temperatures detected must be electronically processed to make it significant, excluding, for example, the possibility that the differences detected can be attributed to precision limits of the sensors.

The alarm signal S1 can thus be defined as a first alarm signal S1, and the additional alarm signal S2 can thus be defined as a second alarm signal S2.

Moreover, in the embodiment shown, there is only one indicator 4 and it is designed to receive both the first alarm signal S1 and the second alarm signal S2. The indicator 4 could thus be considered as comprising a first part and a second part of the indicator 4.

In this case, the at least one acoustic and/or luminous indicator 4 is designed to be also activated by the second alarm signal S2.

The first part of the indicator 4 is designed to provide, following receipt of the first alarm signal S1, at least a first piece of information I1 relative to the fact that the catheter 2 is positioned incorrectly. The second part of the indicator 4 could instead be designed to provide, following receipt of the second alarm signal S2, at least a second piece of information I2 relative to the fact that at least one of the sensors has detected a temperature higher than or equal to the limit value.

Each of these pieces of information I1 and I2 is provided in the form of at least one acoustic and/or visual indication by the indicator 4. The acoustic and/or visual indications which provide the first piece of information I1 and the second piece of information I2 are shown in FIG. 2 by the respective arrows emerging from the indicator 4.

If the indicator 4 comprises a monitor, the parts of the indicator 4 would be two parts of the monitor.

The device could comprise, instead of just one indicator 4, at least two indicators 4 differing in that they respectively provide the first piece of information I1 and the second piece of information I2.

Thus, if there is more than one indicator 4, each one would be configured to receive at least one of the alarm signals S1 or S2, and to provide at least one respective piece of information I1 or I2, in the form of at least one respective acoustic and/or visual indication.

The indicator 4 could also be an integral part of the control unit C, and/or positioned on the control unit C. To receive the alarm signal S1 or S2, the indicator 4 is in any case connected to the control unit C by connection means not shown, such as for example one or more connectors.

The invention described above achieves the proposed aims and allows construction of a system that makes it possible to safely monitor or check the correct positioning of the temperature sensors during cardiac ablation procedures by heating or cooling. The control or monitoring of this positioning can take place at time intervals of a few milliseconds, and thus continually, during the ablation procedures, without involving any risks for the health of the patient undergoing the procedure.

From a practical point of view, the comparative analysis of the signals coming from the sensors must be subjected to filtering and to certain defined tolerance levels, in order not to generate positioning alarms when for example the differences detected by adjacent sensors lie within the precision limits of the sensors themselves.

The invention claimed is:

1. A device (1) for detecting a temperature of an esophagus (E) during cardiac ablation treatments by means of heat transfer or heat removal,
   comprising an esophageal catheter (2) which can be inserted in a patient's esophagus, and
   comprising three or more temperature sensors (3a, 3b, 3c, 3d, 3e) designed to detect a temperature of respective portions of the esophagus,
   each of the three or more temperature sensors being configured to generate, at successive time points, respective detection signals (r) indicating a temperature of the respective portion of the esophagus,
   wherein the three or more temperature sensors are positioned on the esophageal catheter and distributed along a development direction of the esophageal catheter between a first temperature sensor (3a) and a last temperature sensor (3e),
   wherein the device also comprises a control unit (C) configured to be connected to the esophageal catheter when in use and configured to receive the detection signals coming from each of the three or more temperature sensors, characterized in that the control unit is configured to compare, for each of the time points, all the detection signals generated by the three or more temperature sensors (3a, 3b, 3c, 3d, 3e) with each other, and wherein the control unit is configured to generate at least one alarm signal (S1), intended for a case of ablation by heat transfer, when a maximum temperature from among the temperatures detected by each of the three or more temperature sensors and associated with a same time point is detected only by at least one of the first temperature sensor and the last temperature sensor, or configured to generate at least one alarm signal (S1), intended for a case of ablation by heat removal, when the minimum temperature from among the temperatures detected by each of the three or more temperature sensors and associated with the same time point is detected only by at least one of the first temperature sensor and the last temperature sensor.

2. The device according to claim 1, wherein the device comprises at least one acoustic or luminous indicator (4) connected to the control unit and designed to be activated by the at least one alarm signal generated by the control unit.

3. The device according to claim 2, wherein the control unit is configured to generate at least one further alarm signal (S2) when at least one temperature detected by at least one of the three or more temperature sensors is equal to or higher than or equal to or lower than a respective preset maximum or minimum limit value, the at least one acoustic or luminous indicator being designed to be activated also by the at least one further alarm signal.

4. The device according to claim 1, wherein the three or more temperature sensors are aligned in such a way as to form at least one row of sensors along the esophageal catheter development direction.

5. The device according to claim 1, wherein all the three or more temperature sensors are equidistant along the development direction.

6. The device according to claim 5, wherein a distance between one sensor and a next sensor, along the development direction, is between 0.5 cm and 2 cm, the three or more temperature sensors not necessarily being equidistant.

7. The device according to claim 1, wherein a distance between the first and the last sensor, along the development direction, is between 3 and 8 cm.

8. The device according to claim 1, wherein the esophageal catheter is not equipped with ablation elements.

9. The device according to claim 1, wherein each of the three or more temperature sensors is associated with at least one transducer to generate at least the detection signals.

* * * * *